United States Patent
Clark et al.

(10) Patent No.: US 6,436,722 B1
(45) Date of Patent: Aug. 20, 2002

(54) DEVICE AND METHOD FOR INTEGRATED DIAGNOSTICS WITH MULTIPLE INDEPENDENT FLOW PATHS

(75) Inventors: Scott M. Clark, Cape Elizabeth; Robert H. Suva, Windham; Michael R. Kepron, Standish; Stanislaw Barski, Jr., Limerick; Erwin F. Workman, Jr., Cape Elizabeth, all of ME (US)

(73) Assignee: Idexx Laboratories, Inc., Westbrook, ME (US)

( * ) Notice: Subject to any disclaimer, the term of this patent is extended or adjusted under 35 U.S.C. 154(b) by 0 days.

(21) Appl. No.: 09/551,496

(22) Filed: Apr. 18, 2000

(51) Int. Cl.[7] ............... G01N 33/543; G01N 33/53; G01N 33/00
(52) U.S. Cl. .............. 436/518; 436/43; 436/55; 436/169; 436/178; 436/512; 436/524; 436/527; 436/528; 436/536; 436/541; 435/6; 435/7.1; 435/7.92; 435/174; 435/176; 435/177; 435/287.1; 435/287.2; 435/287.3; 435/287.7; 435/288.1; 435/288.7; 422/50; 422/55; 422/56; 422/58; 422/63; 422/68.1; 422/83; 422/88; 422/102; 422/119; 422/255; 422/256; 422/261; 422/283; 422/919; 422/947
(58) Field of Search ............... 422/50, 55, 56, 422/58, 63, 68.1, 83, 88, 102, 119, 255, 256, 261, 283, 919, 947; 435/6, 7.1, 7.92, 174, 176, 177, 287.1, 287.2, 287.3, 287.7, 288.1, 288.5, 288.7; 436/43, 55, 169, 178, 512, 518, 524, 527, 528, 536, 541

(56) References Cited

U.S. PATENT DOCUMENTS

| | | | |
|---|---|---|---|
| 4,343,896 A | | 8/1982 | Wolters et al. ............... 435/7 |
| 4,468,470 A | | 8/1984 | Aalberse ..................... 436/539 |
| 4,603,114 A | * | 7/1986 | Hood et al. .................. 436/89 |
| 4,664,812 A | * | 5/1987 | Klein .......................... 210/679 |
| 4,870,007 A | | 9/1989 | Smith-Lewis ................ 435/28 |
| 4,891,313 A | | 1/1990 | Berger et al. ................. 436/7 |
| 4,923,680 A | | 5/1990 | Geiger et al. ................. 435/7 |
| 4,940,527 A | * | 7/1990 | Kazlauskas et al. ......... 204/401 |
| 4,945,042 A | | 7/1990 | Geiger et al. ................. 435/7 |
| 4,981,786 A | * | 1/1991 | Dafforn et al. ............... 435/7 |
| 5,073,484 A | | 12/1991 | Swanson et al. ............. 435/7.92 |
| 5,141,850 A | | 8/1992 | Cole et al. ................... 436/525 |
| 5,164,294 A | * | 11/1992 | Skold et al. .................. 435/7.5 |
| 5,185,127 A | | 2/1993 | Vonk .......................... 422/56 |
| 5,458,852 A | | 10/1995 | Buechler ..................... 422/56 |
| 5,567,615 A | * | 10/1996 | Degen et al. ................. 435/280 |
| 5,622,870 A | * | 4/1997 | Sizto et al. .................. 436/165 |

(List continued on next page.)

FOREIGN PATENT DOCUMENTS

WO 99/46591 9/1999

Primary Examiner—Mary E. Ceperley
Assistant Examiner—Kartic Padmanabhan
(74) Attorney, Agent, or Firm—McDonnell Boehnen Hulbert & Berghoff

(57) ABSTRACT

Invention performs an assay to determine presence or quantity of specific analyte in fluid sample. Representative device has two separate flow paths established sequentially in device with a single user activation step. First flow path delivers sample, and conjugate soluble binding reagents to solid phase. If analyte is present, an analyte:conjugate complex is formed and immobilized. Sample volume delivered by first path determined by absorbent capacity of solid phase, and not by amount of sample added to device. User need not measure sample volume. Sample/conjugate mixture is prevented from entering second flow path because capillary and surface energy of second flow path prevent it from being wetted by this mixture. Second flow path allows wash reagent to remove unbound conjugate and sample from solid phase to the absorbant, and optionally deliver detection reagents. Adaptable for many formats including, sandwich immunoassays, colloidal gold, sol particle, heterogeneous generic capture, and competitive assays.

14 Claims, 10 Drawing Sheets

U.S. PATENT DOCUMENTS

| | | | |
|---|---|---|---|
| 5,627,026 A | 5/1997 | O'Connor et al. | 435/5 |
| 5,654,162 A | 8/1997 | Guire et al. | 435/7.92 |
| 5,726,010 A | 3/1998 | Clark | 435/5 |
| 5,726,013 A | 3/1998 | Clark | 435/5 |
| 5,744,096 A * | 4/1998 | Jones et al. | 422/58 |
| 5,750,333 A | 5/1998 | Clark | 435/5 |
| 5,885,527 A | 3/1999 | Buechler | 422/58 |
| 6,037,127 A * | 3/2000 | Ebersole et al. | 435/6 |
| 6,171,870 B1 | 1/2001 | Freitag | 436/518 |

* cited by examiner

FIGURE 5
A
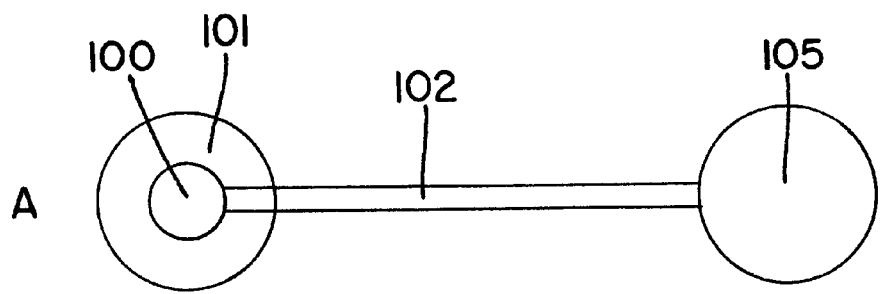
B
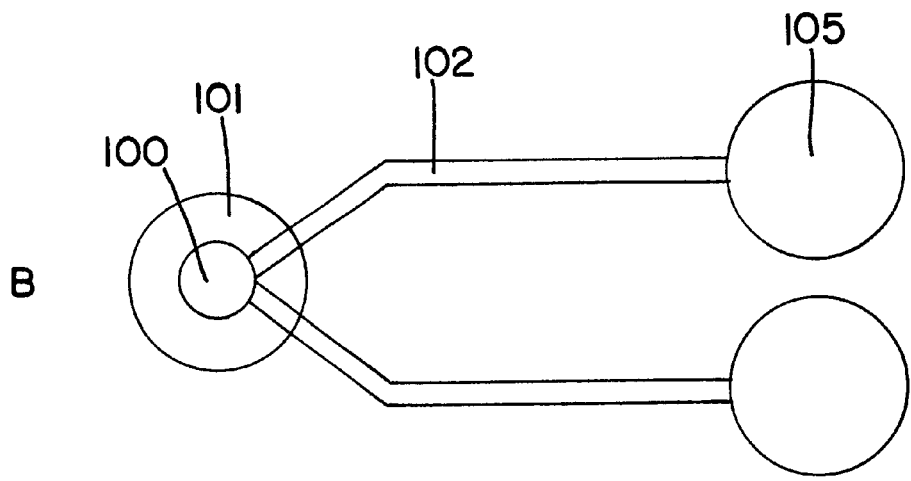
C
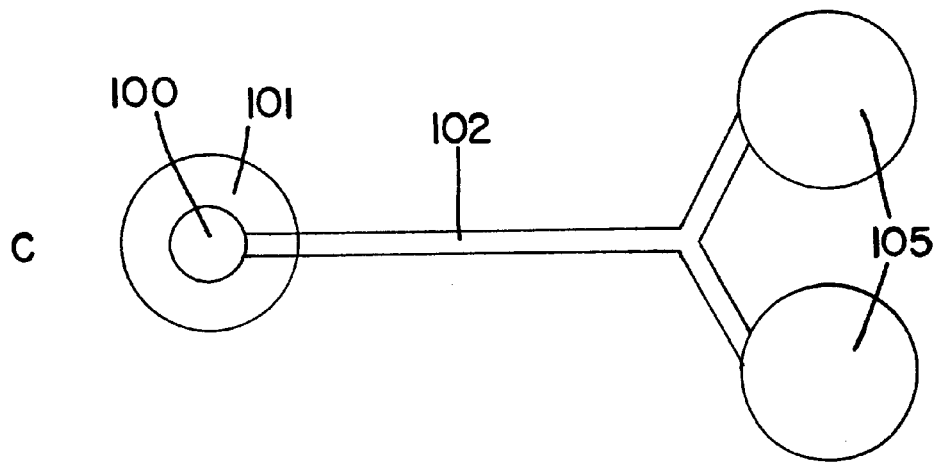

FIGURE 6
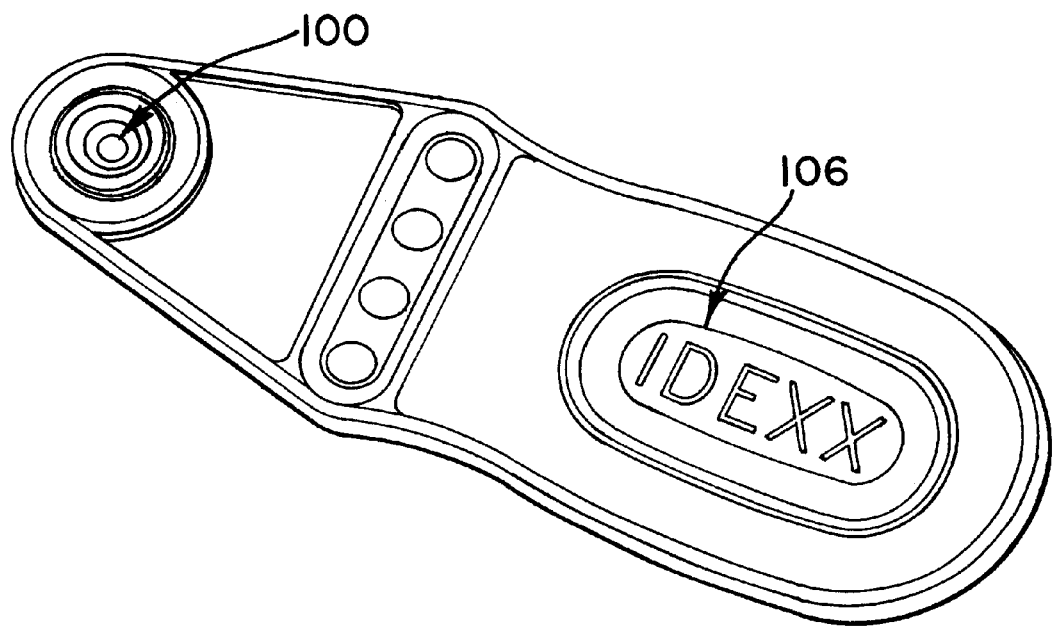
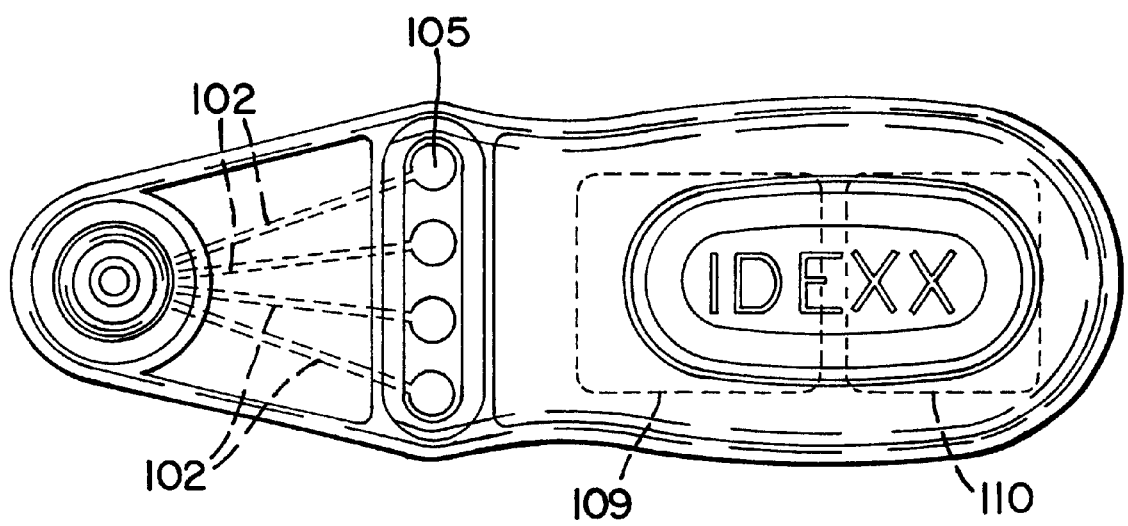

FIGURE 8
CHTW 1
Strong Heartworm Positive
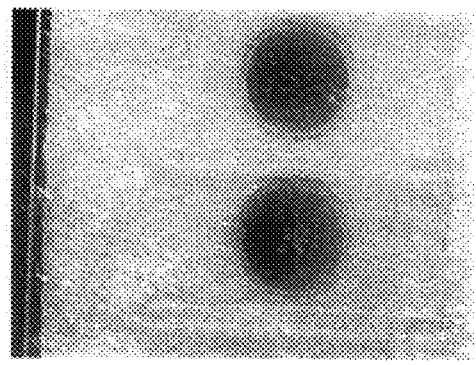
CHTW 3
Weak Heartworm Positive
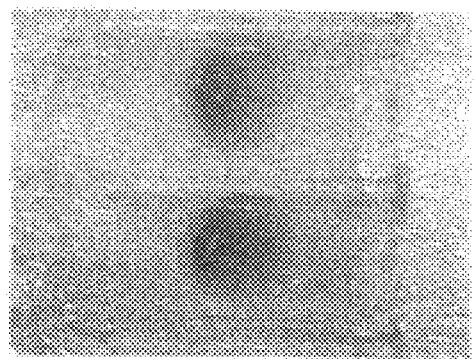
CHTW 4
Heartworm Negative
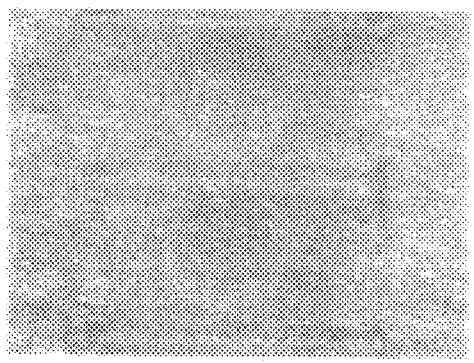

DEVICE AND METHOD FOR INTEGRATED DIAGNOSTICS WITH MULTIPLE INDEPENDENT FLOW PATHS

BACKGROUND OF THE INVENTION

1. Field of the Invention

This invention relates to devices and methods for performing assays to determine the presence or quantity of a specific analyte of interest in a fluid sample. Devices of this invention assay a measured amount of sample employing at least two separate and distinct flow paths which are initiated simultaneously with a single user activation step. These paths are timed for the sequential delivery of assay reagents to the reaction zone, followed by wash or substrate and wash reagents to that zone. These inventive devices and methods may be used for qualitative, semi-quantitative and quantitative determinations of one or multiple analytes in a single test format. They may be practiced with ELISA, sol particle and other assay formats, and are particularly suitable for simultaneous multiple analyte assays. These inventive devices and methods provide for the controlled, self delivery of reagents with no timed steps, and minimal user intervention, in most instances a single activation step.

2. Background

Many prior art assay devices and systems require the user to measure or control the amount of sample added to the device, for example, by dilution. Many prior art assays and systems also require the user to perform a timed sequence of steps and/or to make multiple physical interventions to the device in order to perform the assay.

Buechler et al., U.S. Pat. Nos. 5,458,852 and 5,885,527 (1995 and 1999, respectively), disclose diagnostic devices which do not use porous membranes. In assay methods using such devices, fluid flow is unidirectional and reaction and detection occur in distinct zones. Excess sample/conjugate mixture is used to wash the detection zone. The use of a separate, non-sample wash is not taught or suggested, limiting the versatility of assays of this invention. Likewise, Buechler does not teach or suggest the creation of a second flow path. The time gate in Buechler functions as a delay mechanism in a fluid path, not to redirect fluid flow or to permit different fluids to flow sequentially through a reaction zone. The methods and devices of Buechler et al. do not allow one to use multiple reagents, different wash and substrate reagents and cannot be used in an enzyme amplified assay.

Vonk, U.S. Pat. No. , 5,185,127 discloses a filter stack comprising a hydrophilic membrane (containing a binder for an analyte) above a hydrophobic membrane above an absorbent material. The membrane is impermeable to the sample but permeable to a wetting agent (e.g. acetone, surfactants, detergents, or alcohols, most preferably methanol) mixed with the sample. Sample is added to the device and trapped above the hydrophobic member. Thereafter the wetting agent is added, which when mixed, allows the sample mixture to permeate into the absorbent material. Wash and substrate may be added. Other disadvantages of this device are that it (1) does not teach or suggest a defined fluid path for residual sample or wash, (2) does not permit controlled delivery of predetermined amounts of reaction components or wash, and (3) does not permit sequential delivery of such components.

Clark, U.S. Pat. Nos. 5,726,010, 5,726,013 and 5,750,333 (1998) describes assay methods and devices that use the formation of a solid phase bound tertiary complex to detect an analyte of interest in a fluid sample. A key feature of Clark is the use of a reversible flow in a chromatographic binding assay. An analyte-containing solution is applied to the device and then is transported by capillary flow, first in one direction and then in the opposite direction, along an elongated flow matrix. The flow matrix includes four different regions. Region one is where the analyte-containing solution is mixed with a labeled antibody. Region two, also called the detection zone, contains the second antibody, which is immobilized to a solid phase. Region three contains a site to apply a wash solution. Region four contains an absorbent reservoir located near region one and makes the flow go in the opposite direction. A means to detect the presence or quantity of an analyte is also included in the device. Clark does not automate steps. The user must measure the sample volume, apply it to the device, monitor and control timers, and physically activate the device. The mechanism for reversing flow does not allow for automated timing.

Assays and devices of the present invention overcome the shortcomings of the prior art and offer maximum results without user sample measurement or intervention beyond a single activation step. Assays of this invention may be particularly adaptable to situations where simultaneous detection of multiple analytes in a sample is desirable. Assays of this invention are in a unit dose format, stable, capable of room temperature storage, reliable, easy to manufacture and use, and available for a low cost per test. They have fully integrated packaging for both liquid and dried reagents. In addition, the claimed devices are self-timing for the delivery of reagents so there is minimal operator involvement.

DEFINITIONS

Analyte—The molecule to be detected. For example, an analyte as used herein, may be a ligand, a single compound or a plurality of compounds that share at least one epitopic site to a receptor or an antibody.

Capillarity—The movement of a liquid in contact with a solid that results due to adhesive and cohesive forces and surface tension. Capillarity can be affected by the solid surface, the liquid surface, or both.

Hydrophobic surface—Any surface not effectively wetted by water or an aqueous sample.

Hydrophillic surface—Any surface wetted by water or an aqueous sample.

Conjugate soluble binding reagent—Reagent(s) deposited and dried on a solid support, i.e., the sample delivery channel, and have a specific binding affinity for or chemical reactivity with the analyte of interest. Upon sample application, the conjugate soluble binding reagent becomes dissolved and can begin to flow. Conjugate soluble binding reagent can react with analyte, if present in the sample. Depending upon the assay format, one conjugate soluble binding reagent can be labeled with a detectable label and another with a binding reagent. These different assay formats will be described in more detail below.

Solid phase zone—A material or a surface at the intersection of at least two fluid flow paths.

Sample/conjugate mixture—The liquid mixture comprising the sample solution and solubilized conjugate binding reagents.

Immobilized capture reagent—A molecule that is bound to a solid support and has a specific binding affinity for or chemical reactivity with either the analyte of interest, or can be a receptor for one of the conjugate reagents e.g. avidin.

Sample delivery channel—The hydrophilic means where the conjugate soluble binding reagents are dried and the means through which the liquid sample flows.

Socklet—The hydrophilic mesh material that contains the solid phase when a particulate solid phase is used.

Solid phase—The hydrophilic material to which the immobilized capture reagent is bound.

Second fluid path material—The hydrophobic material that provides the secondary flow path. Examples of second fluid path material are bibulous material, plastic, or any other hydrophobic polymers. As the surface active agent-containing wash solution flows through the second fluid path material, the surface tension is reduced and allows sample/conjugate mixture to flow through the second fluid path material, which is now rendered hydrophilic.

Wash reagent—A liquid reagent that serves to remove unbound material from the solid phase region. As used herein, the wash reagent contains a surface active agent, such as a surfactant, or any other component capable of allowing the wash to wet a hydrophobic surface. Some other examples of wash reagents are alcohol, e.g. methanol, or any other water miscible organic solvents.

Substrate reagent—A liquid reagent that serves to facilitate analyte detection by causing a detectable color reaction. A secondary function of substrate reagent is to remove unbound material from the solid phase region.

Wash/substrate reagent—In some embodiments of the present invention, the wash reagent may also contain a detection agent so that a single solution is delivered via said second flow path to the solid phase zone.

Fluidic bridge—The fluid flow connection that is established between the socklet, second fluid path material and the absorbent reservoir. The fluidic bridge enables liquid flowing in the second flow path to go into the absorbent reservoir.

Lance/wick—A component that is capable of piercing the seal of the liquid reagent containers, i.e., the wash and substrate reagent containers or the combined wash/substrate reagent container. The lance may also include a wick, which facilitates the flow of the liquid reagents out of their storage containers and into the second fluid path material.

SUMMARY OF INVENTION

The present invention is directed to devices and methods for performing an assay to determine the presence or quantity of a specific analyte of interest in a fluid sample. Devices according to this invention comprise a solid phase capable of capturing the analyte of interest after washing unbound material from the solid phase. In one aspect of the device two separate flow paths are established sequentially in the device with a single user activation step. The first flow path delivers the analyte of interest (if present in the sample) and conjugate soluble binding reagents to the solid phase. If analyte is present, an analyte:conjugate complex is formed and immobilized.

The volume of sample delivered by this first path is determined by the absorbent capacity of the solid phase, and not by the amount of sample added to the device, relieving the user from the necessity of measuring the sample. The sample/conjugate mixture is prevented from entering the second flow path because the capillarity and the surface energy of the second flow path prevent it from being wetted by this mixture.

The second flow path allows a wash reagent to remove unbound conjugate and sample from the solid phase to the absorbant, and optionally to deliver detection reagents. The flow of wash reagent along the second flow path is initiated by user activation of the device immediately after addition of sample to the first flow path. When wash reagent migrates to the solid phase, and flows through and around it, it removes unbound reagents and carries them to the absorbent. As a result, the incubation time of the sample and reagents in the solid phase is determined by the flow time of the wash reagent along the second flow path, relieving the user of the requirement to intervene at a specific time.

In one embodiment, the first flow path consists of a sample entry port, a filter element to remove particulates, an open capillary channel containing dried reagents, and a particulate solid phase. The second flow path intersects the first, and consists of a wash reservoir, an absorbent block, and a second fluid path material that extends from the reservoir, contacts the solid phase and finally contacts the absorbent. Sample is prevented from flowing into the second fluid path and absorbent because the surface energy of the second fluid path material is low relative to the sample surface tension, rendering it hydrophobic. The wash solution contains surfactant that allows it to wet the second fluid path material, and thus allow the sample-binding reagent mixture from the solid phase to also flow into the second fluid path material.

The invention may be adapted to many assay formats including, sandwich immunoassays, colloidal gold, or sol particle assays, heterogeneous generic capture assays and competitive assays.

In one embodiment, sandwich assays can be performed by immobilizing an analyte binding reagent on the solid phase, and drying a labeled analyte binding reagent in the first flow path. In a competitive assay embodiment, the first flow path would contain labeled analyte that is dissolved by the sample, and the analyte binding reagent is immobilized on the solid phase. In each of these embodiments, the assay can be further modified to run in a "generic capture" format, where the solid phase binding reagent is instead conjugated to a generic ligand such as biotin, and dried in the first flow path (either together or separately from the other assay reagents), and a generic ligand binding reagent (such as avidin) is immobilized on the solid phase.

Another aspect of the present invention includes a subassembly for the immunoassay device that is comprised of a plastic housing and a means for delivering fluid and/or wash solution, This subassembly comprises a structure formed from a hydrophobic polymer. The hydrophobic polymer has been selectively treated with a water insoluble surface active agent that has been applied as a solution in an organic solvent rendering portions of the surface hydrophilic. When the surface is contacted with an aqueous liquid, it flows only along the treated areas, creating a defined fluid flow path, thereby delivering sample/conjugate solutions to said solid phase.

Another aspect of the claimed device includes a solid phase subassembly referred to as a socklet. The socklet is comprised of a particulate solid phase material that is captured within a structure that is permeable to the sample and liquid reagents, but which prevents the particulate solid phase material from exiting the structure.

BRIEF DESCRIPTION OF THE DRAWINGS

The patent or application file contains at least one drawing executed in color. Copies of this patent with color drawings will be provided by the U.S. Patent and Trademark Office upon request and payment of the necessary fee.

FIG. 5: Schematic depicting some of the alternatives of the present invention for single or multiple analyte testing.

FIG. 6: Three-dimensional view of one of the embodiments of the present invention.

FIG. 8: Photographs of assay results using the embodiment of Example 1.

LIST OF DEVICE COMPONENTS

Figure 9:
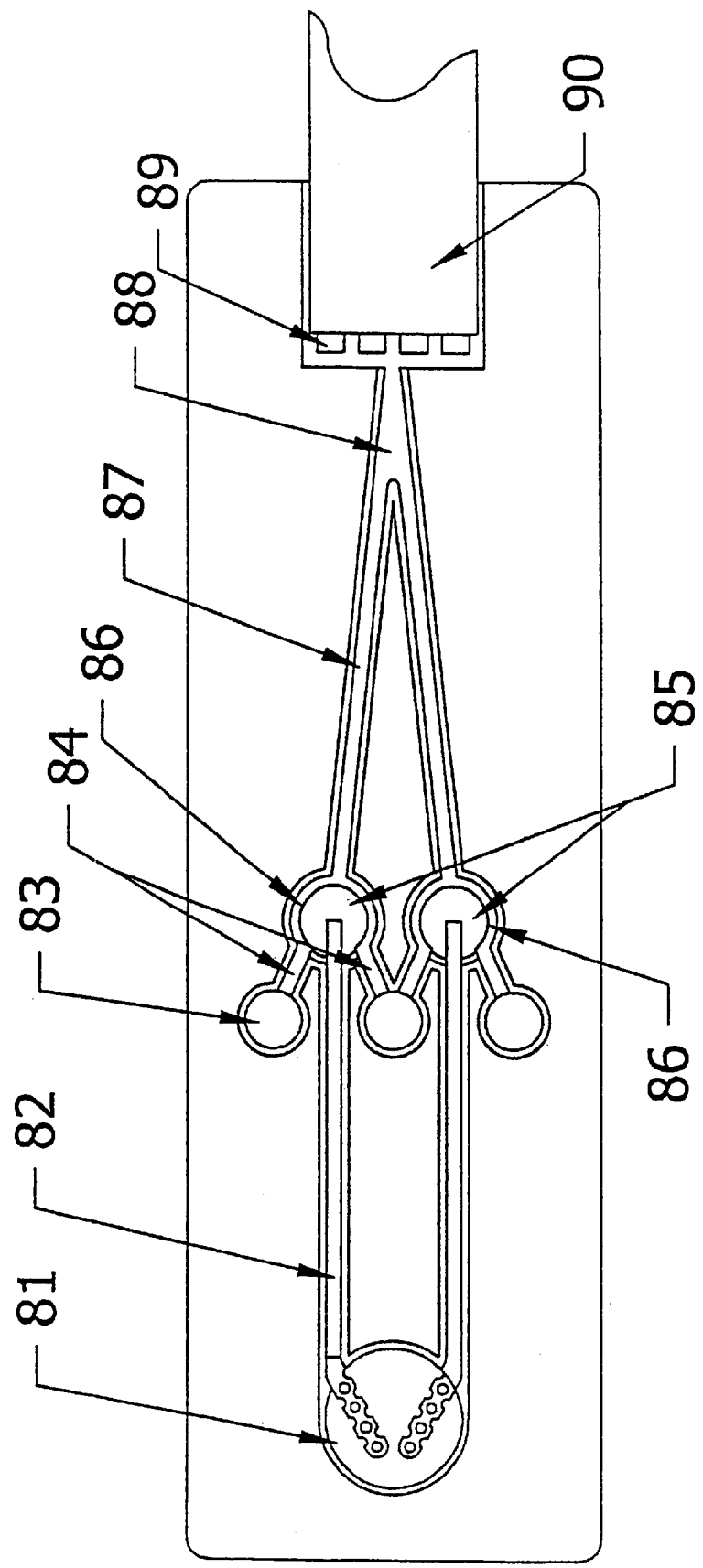
FIG. 9: Schematic depicting another embodiment of the present invention.
Figure 10:
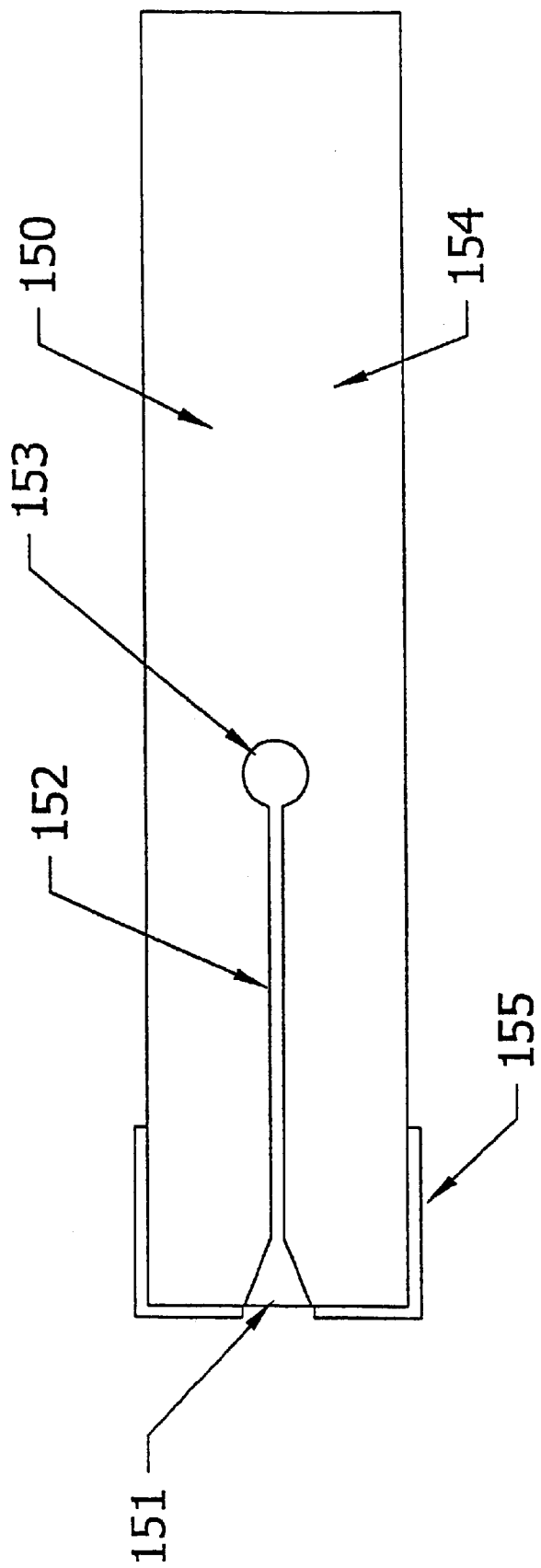
FIG. 10: Schematic depicting another embodiment of the present invention.

81—Sample entry port of device incorporating embodiment of FIG. 9
82—Sample delivery/capillary channel of device incorporating embodiment of FIG. 9
83—Holes through which wicks of device incorporating embodiment of FIG. 9 are inserted
84—Hydrophobic exit channels of device incorporating embodiment of FIG. 9
85—Hydrophilic solid phase material of device incorporating embodiment of FIG. 9
86—Annular cup-shaped hydrophobic space of device incorporating embodiment of FIG. 9
87—Hydrophobic reagent channels of device incorporating embodiment of FIG. 9
88—Hydrophobic channel of device incorporating embodiment of FIG. 9
89—Array of capillary structures of device incorporating embodiment of FIG. 9
90—Hydrophobic bibulous material of device incorporating embodiment of FIG. 9
100—Sample entry port
101—Prefilter
102—Sample delivery channel
103—Conjugate (soluble) binding reagents
104—Socklet
105—Solid phase
106—Activator button
107—Die-cut hole in second fluid path material
108—Second fluid path material
109—Wash reagent
110—Substrate reagent
111—Absorbent
112—Wick
113—plastic housing
114A—Lance
114—Lance
150—Hydrophobic bibulous material incorporating the embodiment of FIG. 10
151—Sample entry port incorporating the embodiment of FIG. 10
152—Sample delivery channel incorporating the embodiment of FIG. 10
153—Solid phase zone incorporating the embodiment of FIG. 10
154—Distal end zone incorporating the embodiment of FIG. 10
155—Absorbant incorporating the embodiment of FIG. 10

Detailed Description of the Preferred Embodiments
Assay Methods

Figure 1:
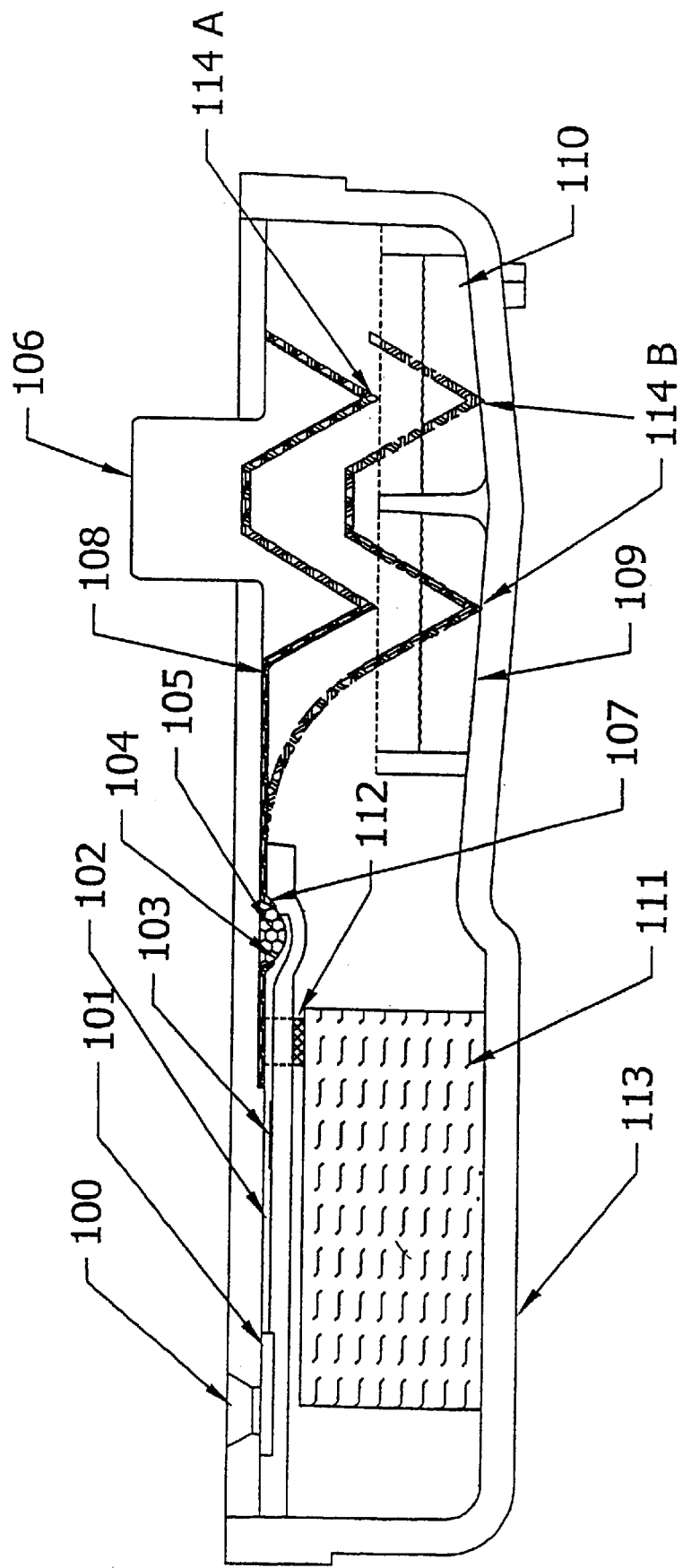
FIG. 1: Side view of one of the embodiments of the present invention.

This invention comprises diagnostic devices and methods to detect the presence of at least one target analyte in a sample. FIG. 1 shows a side view of one of the preferred embodiments of device according to this invention. Generally, the devices of the invention have thicknesses of about 1–30 mm, lengths of about 3–15 cm, widths of about 1–10 cm. Device size is determined by a large number of aesthetic, ergonomic, and performance factors; for example width is affected by number of sample delivery channels 102, length by time to result desired, and thickness is affected by choice of reservoir and absorbent block materials. The device depicted in FIG. 1 shows some of the general features of the devices of the invention. The device comprises various elements: a sample entry port 100, pre-filter 101, one or more sample delivery channel(s) 102, socklet 104, solid phase 105, second fluid path material 108, wash reservoir 109, substrate reservoir 110. Both the wash reservoir 109 and the substrate reservoir 110 have lances 114A & B, which can serve as release mechanisms and wicks.

Referring to FIG. 1, the sample is added to the sample entry port 100 and flows through a pre-filter 101. The sample entry port 100 can be any opening in the device housing for receiving sample and transferring it to the desired location for the start of the assay. Multiple sample delivery channels 102 may also be incorporated into the device. For example, if one sample is being tested for the presence of multiple analytes, once the sample is applied, the device is designed such that equal aliquots are deposited in multiple sample delivery channels. Devices with multiple sample delivery channels will be discussed in more detail below. Once the sample goes through the pre-filter 101, the sample flows into the hydrophilic sample delivery channel 102 where dried conjugate soluble binding reagents 103 are located. When the liquid sample enters sample delivery channel 102 the conjugate soluble binding reagents 103 are dissolved into the sample solution and mobilized. Mixing the sample and conjugate allows the binding reactions to begin. Depending on the assay format complexes may form between binding reagents and analyte in the sample. These binding interactions continue to form while reagents continue to flow through the sample delivery channel 102.

Figure 2:
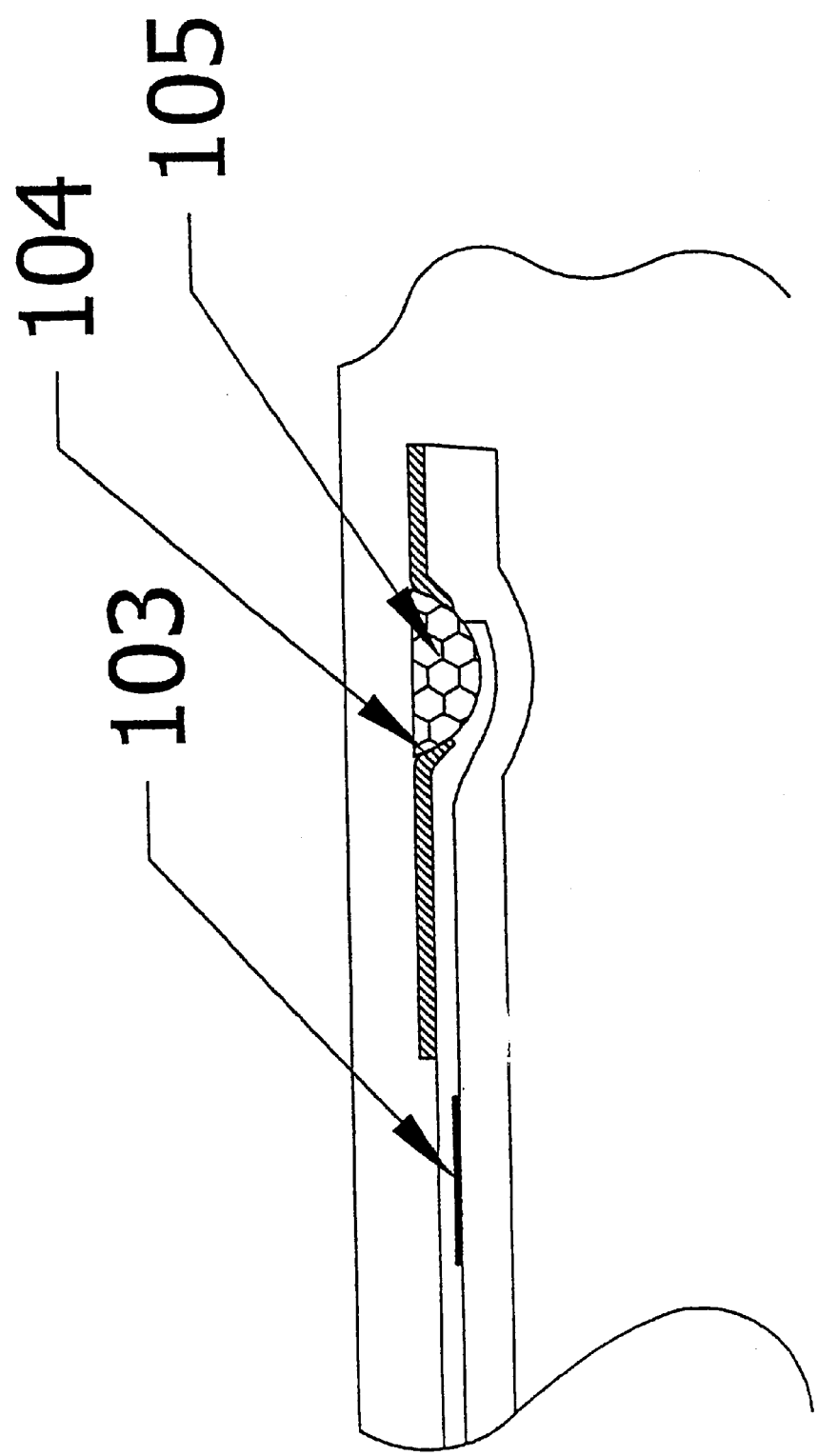
FIG. 2: Exploded side view of the preferred embodiment of the present invention

Once the sample/conjugate mixture reaches the distal end of sample delivery channel 102, the sample/conjugate mixture flows to the solid phase 105. This embodiment uses a socklet 104, a hydrophilic mesh which holds a particulate solid phase material. The invention may be practiced without a socklet, for example when non-particulate solid phase materials are chosen. FIG. 2 depicts the preferred embodiment using socklet 104, which encases solid phase 105. The physical properties of the chosen flow materials, specifically their capillarity and surface energy ensure that the sample/conjugate mixture will be drawn from sample delivery channel 102 into solid phase 105. The saturation of hydrophilic solid phase 105 allows the interaction between the analyte (if present in the sample), conjugate soluble binding reagents 103, (and preformed complexes of these elements), to combine with immobilized capture reagent, which is irreversibly bound to solid phase 105. If the analyte of interest is present in the sample, conjugate soluble binding reagents-analyte of interest-immobilized capture reagent complex is formed and immobilized to solid phase 105.

Once the solid phase is saturated, flow within the first flow path is completed, and flow stops because the solid phase 105 is encased within a second fluid path material 108 which is not wetted by the sample. Second fluid path material 108 thus acts as a "barrier" to the flow of the sample, permitting the sample to only flow within and saturate the first flow path but not enter the second flow path. This second fluid path material 108 is a component of the second flow path. In this manner, the volume of sample tested by the device is precisely controlled by the volume of sample absorbed by solid phase 105. Since the device itself controls the volume of sample tested, the test operator is relieved of the necessity of precision-pipeting the sample.

Saturation of solid phase 105 with sample containing conjugate soluble binding reagent(s) 103 allows the aforementioned binding reactions to occur. The time during which the binding reactions occur is determined by the time the sample mixture is allowed to reside within solid phase 105. The sample residence time is controlled by the arrival of the wash solution 109 flowing within the second fluid path material 108 of the second flow path.

Figure 4:
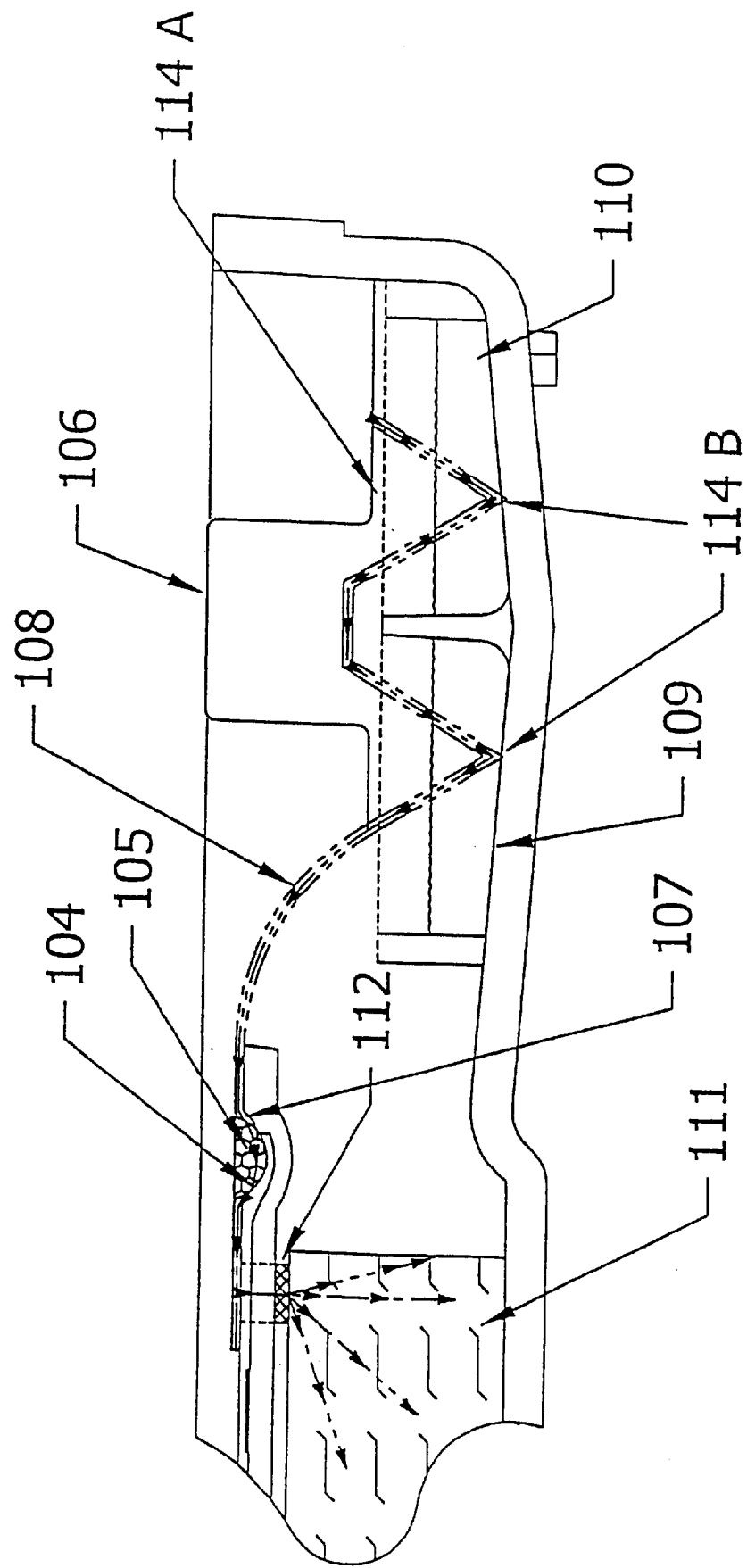
FIG. 4: Schematic of second flow path of the preferred embodiment of the present invention.

The second flow path delivers wash reagent 109 and/or substrate reagent 110 to the solid phase 105 in the following manner. Flow along the second flow path is initiated when the device is activated by pressing the activator button 106. Referring to FIG. 4, the wash reagent 109 and substrate reagent 110 reservoirs are punctured by lances 114A & B and the wash and substrate reagents are simultaneously released. The wash 109 and/or substrate 110 reagents flow into and through the second fluid path material 108 towards the solid phase 105. Although the second fluid path material 108 is initially hydrophobic, the wash reagent 109 is able to wet and flow through this material 108 because the wash reagent 109 contains a surface active agent which changes the surface tension of the second fluid path material 108, "converting" the second fluid path material 108 into a hydrophilic material, thus, allowing the wash reagent 109 to flow. When the wash reagent 109 reaches socklet 104, a portion of wash reagent 109 continues to flow along the second fluid path material 108, past the socklet 104, through the wick 112 and into the absorbant 111. In this manner, a flow bridge between the socklet 104 and the absorbant 111 is established, utilizing the second fluid path material 108 now made hydrophillic by the wash solution. This fluidic bridge eliminates the "barrier" between the second flow path and socklet 104 allowing sample and unbound reagents contained within socklet 104 to flow into absorbant 111. Once the second flow path is established, efficient washing of solid phase 105 occurs because wash reagent 109 flows over, around, and through solid phase 105, and allows sample and unbound reagents within solid phase 105 to flow into absorbant 111.

Figure 3:
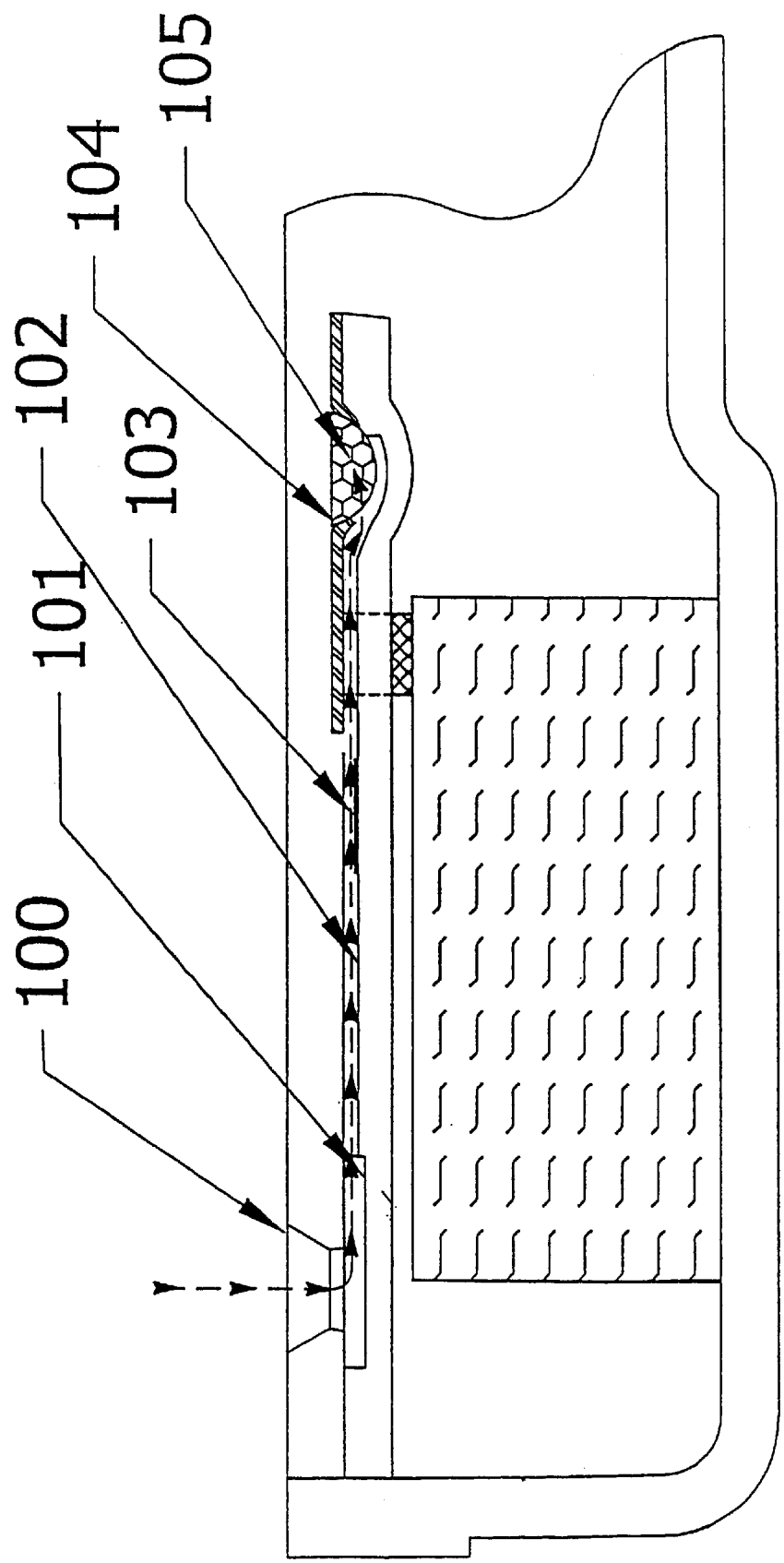
FIG. 3: Side view schematic of first flow path of the preferred embodiment of the present invention.

FIG. 3 depicts the first flow path in more detail. The arrows show the flow path after sample addition to sample entry port 100. FIG. 4 depicts the second flow path in more detail. FIG. 4 is a side schematic view of the second flow path with arrows to depict fluid movements. In this embodiment, when the second fluid path material 108 is rendered hydrophilic, residual sample from the sample delivery channel 102 is drawn into absorbent 111 because a portion of the second fluid path material 108 is in contact with sample delivery channel 102.

The interaction between the materials selected for the first and second flow paths is important for creating the second flow path. Once the boundary between the fluid paths is removed, absorbent block 111 provides sufficient capillarity to pull the reagents into absorbent 111 and sustain a separate second flow path that flows in a second direction from the first flow path. Delivering a liquid from this new direction controls the opening of the boundary between the flow paths.

The wash step is critical for the elimination of any unbound reagents to reduce non-specific binding and thereby increase assay performance. This device of the claimed invention is designed to enable the controlled delivery of a clean wash solution. In one preferred embodiment, this controlled delivery is dependent on the placement of (i.e., the distance between) solid phase 105 and the wash reservoir.

In another preferred embodiment, the device can be manufactured in several different ways to engineer the opening of the boundary between the flow paths by the wash solution, without regard to the placement of solid phase 105. For example, one may engineer a flow path around the solid phase contact zone rather than underneath the solid phase. There are many ways to engineer the second flow path to ensure that some wash/substrate reagent reaches the absorbent and therefore can initiate sample washing.

If the conjugate soluble binding reagents 103 require a substrate, e.g. if horse-radish peroxidase is used, the substrate reagent follows the flow path of the wash reagent. The color that develops at the solid phase is proportional to the level of analyte of interest present in the sample. Alternatively, the detector conjugate binding reagent 103 used does not require a substrate e.g. conjugated to colloidal gold or fluorescent tag, or an electrochemical detector. In this case, the substrate reservoir would not be included as part of the device.

In yet another alternative embodiment to FIG. 1 the device can be modified to allow detection of the analyte on an electrochemical sensor. The solid phase 105 and socklet 104 are replaced by a set of electrodes (working, counter, and reference electrodes) printed in a recess on the solid phase carrier part. Printed conductive pathways extend to the end of the device. Sample delivery channel 102 drains into a capillary space created in the part over electrode (optionally containing capillarity-inducing materials or structures). The hydrophobic bibulous material 108 comprises the top of the space. The immobilized reagents 103 are attached to the surface of the working electrode.

In this alternative embodiment to FIG. 1, sample applied to the entry port 100 migrates through the pre-filter 101 and along the sample delivery channel 102, dissolving conjugate soluble binding reagents 103. The sample/conjugate mixture flows into the space above the electrodes, where flow stops and binding reactions take place. Activation of the device initiates flow of wash solution along the second fluid path material 108. When the wash reaches the area above the electrodes, the sample solution containing unbound analyte is drawn into the second flow path and removed to the absorbant 111. Additional wash reagent 109 flows through the space above the electrode, efficiently removing unbound reagents. If needed, a substrate reagent 110 flows sequentially along the second flow path, providing additional detection reagents. The amount of bound analyte is detected electrochemically. The electrodes could be printed on an electrode cover part, and the first fluid path would pass through a die-cut hole 107 in the second flow path material 108. Additionally, other detection methods that depend on a surface could be applied to this device. For example, if the parts were made of transparent material, surface plasmon resonance could be measured on the binding surface.

DEVICE COMPONENTS

Sample Entry Port

The sample entry port 100 is an opening in the plastic housing through which the sample is added. In one embodiment, sample entry port 100 is located upstream of solid phase 105. There are different ways that a sample may be applied to the invention device. One example of a sample entry involves a cup structure comprising a raised surface surrounding the sample entry port provided on the top of the device. In this example, sample is dropped into the cup structure from a dispensing device, such as a piptettor or a syringe. The cup structure serves to contain the sample around sample entry port 100. In another example, the sample may be applied to the device using a sample absorbing tip. In this example, a narrowed end of the device is adapted to directly absorb sample into the device. Liquid permeable fluid channels are provided within the device to transfer the sample from the tip of the device to sample delivery channels 102. The advantage of this example is that no dispensing device is required to aliquot sample. In this example, the total volume of channel structures and solid phase contained within the device controls the volume of sample required.

Pre-Filter

Sample entry port 100 may or may not contain pre-filter 101. If the device of the present invention includes pre-filter 101, its primary function is to remove any large particulate matter, which could clog the device and potentially interfere with the assay results. Pre-filter 101 pores need not be small enough to remove blood cells if the remainder of the device is compatible with whole blood. However, if blood cells need to be removed, or additional separation is desired, the pre-filter 101 used may be one available in the art for this purpose. In the preferred embodiment a single layer of hydrophilic medium is used.

In the preferred embodiment for multiple analyte testing, the sample moves through the pre-filter 101 into several sample delivery channels 102. Each channel 102 contacts the pre-filter 101, but the channels 102 are otherwise independent from each other. This independence minimizes fluidic interaction and cross-contamination of reagents between independent assays. Many alternatives are possible, depending on the type of assay desired.

Sample Delivery Channel

In the preferred embodiment, the first flow path consists of a hydrophilic sample delivery channel 102 that contains dried conjugate soluble reagents 103. Although the preferred embodiments include dried conjugate soluble reagents in the sample delivery channel, some embodiments of the invention include the addition of conjugate soluble reagent(s) to the sample before it is added to the device. The geometry and surface treatment of the sample delivery channel 102 are designed to control the time of transit of the sample from pre-filter 101 to the solid phase 105. For example, plastic capillary channels can be made hydrophilic by corona treatment or by treatment with a water-insoluble surfactant. The first flow path may also consist of other materials, including bibulous materials such as single or multiple conventional immunoassay strips containing dried conjugate binding reagents.

The sample delivery channel 102 may be designed to produce sufficient capillarity to pull sample from the pre-filter into the sample delivery channel. In this case, the overall capillarity of each of the components, pre-filter 101 and sample delivery channel 102 must be taken into account when designing the system so that the sample flow is in the direction of sample delivery channel 102. In this case, the system is active, in that fluid flow is determined by the physical characteristics of the device and its components, rather than relying on an external force to induce fluid flow.

The primary functions of the sample delivery channel are to serve as a repository for conjugate binding reagents 103 and ensure that they are distributed evenly throughout the sample, and to serve as a conduit for the sample/reagent mixture to the solid phase. The design of sample delivery channel 102 is important to provide even distribution of the conjugates. In some embodiments it may be desirable to promote mixing of the sample as it passes through the conjugate channel by incorporating surface topography into the parts.

In a generic capture system, the sample delivery channel may have two different reagents deposited and dried in the channel. The reagents are a first immunological binding reagent to which a detectable label has been attached (the conjugate) and a second immunological reagent to which a receptor molecule has been attached.

Solid Phase Material

The solid phase 105 contains a material coated with a reagent to blind the reaction products formed by the binding reagents and the analyte. Solid phase materials may be glass fiber mats, non-woven synthetic mats, sintered particulate structures, cast or extruded membrane materials, or other materials characterized by the presence of adhesion within the material. The solid phase 105 may be a formed (molded or cast) open pore structure such as nylon or nitrocellulose. The solid phase 105 may also be a particulate material such as glass particles or polymer particles. The solid phase 105 may also be a surface (such as an electrode or another sensing surface) with a defined fluid space bordered by the surface and the flow path material.

The solid phase materials may be slit, cut, die-cut or punched into a variety of shapes prior to incorporation into the device. Biological reagents may be applied to the materials before or after forming the desired shape. Biological reagents may be attached to the materials either passively or covalently. Examples of alternative shapes of the solid phase assemblies maybe circular, square/rectangular-shaped, flattened ellipse shaped or triangularly shaped.

In another embodiment, the solid phase 105 is a particulate material, which is not pre-formed into a structure that contains internal adhesion. In this embodiment, the particulate solid phase 105 is captured within a socklet. In this embodiment, the solid phase material is selected from the group consisting of inorganic or organic particulates, glass beads, polymer particles. In the case of a sandwich immunoassay, a preferred solid phase matrix is glass beads covalently coated and with avidin, which is the receptor-binding partner to a biotinylated binding reagent.

Socklet

Socklet 104 is a hydrophilic mesh material which physically captures solid phase 105 without impeding the flow of liquids. In this particular embodiment, socklet 104 is permeable to the sample and liquid reagents, but does not allow the particulate solid phase material to exit the structure.

Second Fluid Path Material

In one embodiment, the second fluid path material 108 is defined by a hydrophobic medium that can be comprised of bibulous material, plastic, non-woven polyester fiber material, or any other hydrophobic structure formed to provide a path for sample/reagent flow. In the preferred embodiment, a porous second fluid path material 108 is placed in contact with a wash reservoir, extends to contact solid phase 105 and extends further to wick 112 and absorbent 111. The second fluid path material 108 surrounds the socklet 104 encased solid phase 105 (refer to FIG. 1). A die-cut hole 107 in second fluid path material 108 allows sample to travel from the sample delivery channel 102 to solid phase 105. In the case of multiple solid phase 105 assemblies, the respective number of die-cut holes 107 will be made in the second fluid path material 108 to allow delivery of the samples through the second fluid path material 108 into solid phase 105.

In the preferred embodiment, the second fluid path material 108 also serves as a fluid conduit for a detection reagent and is constructed in such a way that it ensures that wash reagent 109 flows before substrate reagent 110.

Absorbent

Absorbent 111, serves as an excess reagent reservoir that is capable of accommodating a volume of liquid in excess of the total sample volume and the total volume of all other liquid reagents. In alternative embodiments, the excess reagent reservoir can be a molded vessel for holding excess fluid or a continuation of the second fluid path material that has been folded or otherwise made into an excess reagent reservoir.

Reagent System

The conjugate soluble binding reagents 103 are dried into sample delivery channel 102, and are dissolved by the sample. In the example of a sandwich immunoassay, the preferred reagents include first and second conjugate soluble binding reagents 103. A first conjugate soluble binding reagent 103 may be an antibody (or antigen) conjugated to a detectable label. The detectable label may be a light absorbing particle such as colloidal gold or a colored latex particle, a phosphorescent molecule, a fluorescent molecule or an enzyme, such as horseradish peroxidase. Additionally, the detectable signal can be electrochemical or any other signal used in the art as an assay readout. The second conjugate soluble binding reagent 103 may be an antibody (or antigen) conjugated to a receptor molecule such as biotin. Alternatively, the binding partners for the assays described herein can include antigens, antibodies, ligands, receptors, nucleic acid molecules, chemical reactants, fragments of these, and other such reagents used in the art for conducting assays.

The concentration of conjugate soluble binding reagent(s) 103 in the sample is affected by the rate of dissolution of the conjugate soluble binding reagent(s) 103 by the sample, the flow rate of the sample, and the by amount of conjugate soluble binding reagent(s) 103 applied to sample delivery channel 102.

Further embodiments of the described invention include the assay of enzymatic or chemical reactions by immoblizing a reactant or substrate on solid phase 105, and detecting the product, or by diffusively or non-diffusively immobilizing the reactant or substrate in the first flow path, and detecting the product in the solid phase zone.

Different Embodiments of the Present Invention

In another embodiment, depicted in FIG. 9, the first fluid path consists of a sample entry port 81 in fluidic communication with each of two hydrophilic sample delivery/capillary channels 82 containing dried binding reagents. The distal end of each channel 82 is in fluid communication with the underside of the hydrophilic solid phase material 85.

The second fluid path begins in a piece of hydrophobic bibulous material 90 that is buffed against an array of capillary structures 89 which withdraw wash reagent from hydrophobic bibulous 90 into hydrophobic channel 88. This channel splits into two hydrophobic reagent channels 87, which connect to an annular cup-shaped hydrophobic space 86 around the solid phase 85. Connected to the distal side of this space is a set of hydrophobic exit channels 84 which lead to wicks inserted into holes 83. The wicks are in fluidic communication with an absorbent block under the device (not shown).

In operation, sample enters the port 81, flows down the channel 82 and dissolves the dried reagents. Flow continues down the channel and into the solid phase 85, where flow stops when the solid phase 85 is saturated. The flow of the sample/reagent mixture does not flow into the second flow path because the surfaces of the second flow path are hydrophobic.

Coincident with addition of sample, the device is activated, initiating flow of wash along bibulous material 90. When the wash reaches the array of capillary structures 89, it migrates from the hydrophobic bibulous material 90 and into the hydrophobic channel 88. Flow of the wash splits and continues along reagent channels 87. When the flow reaches annular cup-shaped hydrophobic space 86, a portion of the wash passes around solid phase 85 and into the exit channels 84. Wetting of these surfaces by the wash renders them hydrophilic, and the sample in the solid phase 85 is then drawn into the exit channels 84 and into the wicks 80, followed by the remaining wash. In the case of an enzyme amplified assay, substrate solution would flow sequentially after the wash along the second fluid path.

When the label of one of the conjugate soluble binding reagents is an enzyme, the substrate flows from a reservoir along the hydrophobic bibulous material 90, following the wash reagent. The substrate fluid path follows the wash fluid path, and therefore is part of the second flow path. The assay is complete when the enzyme label in the solid phase 85 has reacted with substrate.

In another embodiment of the invention depicted in FIG. 10, all of the flow paths are created on a single piece of hydrophobic bibulous material 150. As shown in FIG. 10, a strip of hydrophobic bibulous material 150 is printed with a water insoluble surfactant to create a first hydrophilic fluid path consisting of a sample entry port 151, a sample delivery channel 152, and a solid phase zone 153. Sample is applied to sample entry port 151, migrates along the first fluid path, and dissolves conjugate soluble binding reagents deposited in sample delivery channel 152. When sample/conjugate mixture reaches solid phase zone 153, the analyte in the sample and analyte/reagent complexes bind to the immobilized reagent attached to the solid phase zone 153. When solid phase zone 153 (as defined by the limits of application of the water-insoluble surfactant) is saturated, flow stops. Wash reagent containing surfactant is applied (by the operator or by methods described in previous examples) to the distal end zone 154 and migrates along bibulous material 150 rendering it hydrophilic. When the wash reaches solid phase zone 153, it allows the sample solution in solid phase zone 153 to migrate through bibulous material 150, and into absorbant 155. Additional wash migrates through solid phase zone 153, removing all unbound reagents. If a substrate reagent is required, it is applied to distal end zone 154 after the wash, and flows along sequentially after the wash.

Alternatively, this fluid path in this embodiment can be cut from a sheet of hydrophilic bibulous material and bonded to hydrophobic bibulous material 150. The underside of bibulous material 150 is contacted with hydrophilic absorbant 155.

Alternative Structures for Single or Multiple Analyte Testing

FIG. 5A, depicts a single sample entry port 100, single sample delivery channel 102 and a single solid phase 105 assembly. This structure is useful to test a single analyte per sample. No controls are present in this format. Multiple units of this structure may be placed within a single device to perform a single test on multiple samples. The use of multiple channels is very versatile. For example, one could design a colloidal gold sandwich assay side-by-side with an enzyme amplified competitive assay. Alternatively, channels may be used for positive and negative controls.

FIG. 5B, shows a structure with a single sample entry port 100, two separate sample delivery channels 102 and two separate solid phase 105 assemblies. It can be used for testing a single sample for two or more unique analytes or a single sample for a single analyte and a control. Different assay formats may be used simultaneously with this structure. Multiple units of this structure may be incorporated into a single device to test multiple samples for multiple analytes.

FIG. 5C, is an example of a structure with a single sample entry port 100, single conjugate channel 102 and two separate solid phase 105 assemblies. This structure is most useful for use in an immunoassay format where the biological reagent present in the two solid phase 105 assemblies are different, particularly when one solid phase 105 acts as a control for the other.

Operation of the Device

FIG. 6 depicts one embodiment of the claimed invention device. The user adds to the sample entry port 100 a volume of sample at least sufficient to fill the sample delivery channels 102, prefilter 101, and solid phase 105 (about 30 microliters in the examples) and presses activator button 106 to activate the device. The activation process causes the lance/wick to rupture seals on the wash 109 and substrate 110 containers, initiating flow of these reagents. The sample flows through the filter element 101, and into the sample delivery channel 102. The sample dissolves the dried conjugate soluble binding reagents 103, initiating the reaction. The reaction mixture flows into solid phase 105, where the second phase of the binding reaction occurs i.e., immobilization of analyte-conjugate soluble binding reagents complex to solid phase 105. The first flow path stops at the distal end of the solid phase. The incubation time in the solid phase 105 is determined by the transit time of the wash solution 109 along the second fluid path material 108. Wash reagent 109 removes the unbound reactants from the solid phase 105, and substrate 110 flowing sequentially after the wash solution 109 then develops a signal.

OPTIONAL EMBODIMENTS

Other Labels

When the label used is a colored particle e.g., colloidal gold, or a fluorescent or electrochemical tag, a substrate is not required, and the assay is complete after the wash has removed unbound material from the solid phase binding zone.

Semi-Quantitative Assays

In a semi-quantitative assay, it is sometimes desirable to compensate for device and sample variations by comparing the analyte assay signal against that generated in a control reaction. In this case, reagents for a test reaction and a control reaction may be dried together in the sample delivery channel. In this embodiment, the sample delivery channel is then split, feeding two solid phase binding zones, each specific for one of the reactions.

Quantitative Assays

In a quantitative assay, precision and enhanced sensitivity may be achieved by precisely controlling the timing steps of the reaction. The precision of this assay device may be improved by developing an instrument that controls the time that the sample resides in the sample delivery channel, the time the sample/reagent mixture resides in the solid phase, and the time after washing that the assay is read.

EXPERIMENTAL PROCEDURES

Example 1

This example relates to the present methods and devices for the detection of canine heartworm antigen in a sample.

Preparation of anti-heartworn-enzyme conjugate: Horseradish peroxidase (HRP) (20 mg) was oxidized with a 100-fold molar equivalent of sodium periodate at pH 4.5, then mixed with 1.25 equivalent amount by weight of affinity-purified chicken-anti-heartworm antibody. After 1.5 hours of reaction, the HRP-antibody conjugate was stabilized by reduction with a 100-fold molar equivalent of sodium borohydride, incubated for a further 0.5 hours. Conjugate was stored at 1 mg/ml protein concentration in conjugate diluent. This HRP-antibody conjugate is one of the conjugate soluble binding reagents that will be dried in the sample delivery channel of the device prior to use.

Preparation of biotinylated anti-heartworm antibody: Affinity-purified rabbit-anti-heartworm antibody (20 mg) was reacted at alkaline pH with 15 molar equivalents of biotin-amidocaproyl-NHS ester. Unreacted biotin was separated by dialysis. Antibody biotinylation may be determined using standard methods such as avidin binding. This biotinylated antibody is the second conjugate soluble binding reagent that will be dried in the sample delivery channel of the device prior to use.

Preparation of solid phase: 1.4 kg of borosilicate glass spheres (65 $\mu \pm 10$ $\mu$diameter) were stirred for 4 hours with 1.4 L of aqueous 1% aminopropyltriethoxysilane (1 w/v (kg/L) to produce aminopropyl-glass. After washing over a coarse-porosity sintered glass funnel with 5 L of water and curing at 50° C. overnight, 600 g of the aminopropyl-glass was stirred with 50 mL of 4.4% solids carboxyl-latex (87 nm diameter, 430 $\mu$eq/g) in 600 mL of 50 barbituric acid buffer, pH 3.3. The latex was coated to the aminopropyl-glass by stirring 40 mg/mL aqueous EDAC into the glass suspension in two additions of 10 mL spaced 30 minutes apart, then allowed to react for an additional hour. Unbound latex was removed from the resulting latex-coated glass by washing with 2 L of 0.2 M NaCl followed by 8 L of water. To coat the latex-glass with neutravidin, the washed latex-coated glass (600 g) was suspended in 600 mL of 50 mM MES (2-N-(morpholinoethanesulfonic acid)) buffer, pH 6.0 and stirred with 10 mL of 29 mg/mL aqueous neutravidin followed by two additions of 14.5 mL of 40 mg/mL aqueous EDAC spaced 30 minutes apart, then allowed to react for an additional hour. Unbound neutravidin was removed from the resulting neutravidin-latex-glass by washing with 2L of buffer A (50 mM potassium phosphate, 0.1% EDTA, pH 8.0) containing 0.1% Tween 20, followed by 2 L of buffer A containing 0.5 M NaCl, and finally 2L of buffer A.

The described solid phase has several advantages. The pore size determined by the glass particles provides high capillarity while allowing easy flow of blood cells without entrapment. Coating the glass with latex particles increases the surface area, allowing greater amounts of immobilized reagents and thus faster binding reactions. The latex also reduces non-specific binding and provides a surface that allows easily coupling of reagents. Finally, the raw materials are inexpensive, readily available, and allow the preparation of the final solid phase in bulk process.

The assay device was assembled as follows (Refer to FIG. 1):

1. Depositing 5.5 $\mu$l of a slurry of the solid phase 105 into each of two spots on a solid phase carrier and drying to a solid.
2. A pre-formed nylon mesh socklet (Saatitech PA-3121) 104 was heat-staked over the dried solid phase 105.
3. A strip of hydrophobic non-woven polyester (Ahlstrom 6627) 108 with two 0.093" holes was heat-staked over the solid phase 105. This hydrophobic material serves as the second fluid path material 108 of the device.

4. Each sample delivery channel 102 was made hydrophilic by deposition of 680 nl of a 2.5% solution of Brij 72 surfactant in diacetone alcohol using a BioDot Quanti-Biojet.
5. The parts were dried and 212 nl of 50% sucrose were deposited on top of the surfactant layer followed by drying.
6. The chicken anti-heartworm-enzyme conjugate (100 nl, 1 mg/ml) and the biotinylated rabbit anti-heartworm antibody (50 nl, 1 mg/ml) both serving as conjugate soluble binding reagents 103, were deposited into a portion of the sample delivery channel 102 of the part from step 5 and dried.
7. A glass fiber pre-filter (Ahlstrom 8980) 101 was placed over the sample entry port 100, and a plastic cover was ultrasonically welded over the deposited antibodies to make the sample delivery channel assembly 102.
8. The solid phase assembly 105 and the sample delivery channel assembly 102 were attached to each other by heat staking.
9. Absorbent wicks (Filtrona R-14545, bonded polyester/polyethylene, 0.078" dia.) were placed in the holes of the device, and an absorbent cellulose acetate block 111 was held against these wicks.

A serum sample containing canine heartworn antigen was added to the pre-filter of the assembled device. The sample flowed into the sample delivery channels and dissolved. the deposited antibodies, facilitating the reaction of the antibodies with the antigen. The reaction mixture flowed further down the sample delivery channel and into the solid phase, where flow stopped. Biotinylated antibodies in the reaction mixture bound to the solid phase, capturing immune complexes with the antigen and antibody-enzyme conjugate. FIG. 9 depicts the immuno-complex formed in this experiment.

Coincident with the addition of the sample, the end of the strip of hydrophobic polyester is placed in contact with a reservoir containing 250 μl of a surfactant-containing wash reagent containing 0.025 M citrate, 0.15 M NaCl, 0.5% Kathon, 1% Triton X-100. 0.75% Dry milk, 1.5% BSA (from 30% liquid stock). The wash reagent is made to pH 7.0 and filtered through a 0.2 micron filter. The wash reagent starts migrating through the strip of hydrophobic polyester. When the wash reagent reaches the region of the strip of hydrophobic polyester adjacent to the solid phase, it migrates into the solid phase, removing unbound antibodies. The wash continues to migrate through the strip of hydrophobic polyester and into the absorbent wicks and block, bringing the antibody solution along. When the wash reservoir is empty, the strip of hydrophobic polyester is placed in contact with a second reservoir containing 250 μl of TMB substrate solution (Moss, TMBM 1000), which migrates through the strip following the wash. When the substrate reaches the solid phase, it replaces the wash solution and a blue color develops in the solid phase in proportion to the amount of bound antibody-enzyme conjugate. When a similar device was run using a negative serum sample, no visible color developed. See FIG. 10.

| FLOW | TIMES |
| --- | --- |
| Sample to solid phase | 10–15 seconds |
| Wash to solid phase | 30 seconds |
| Sample removal complete | 1 minute 45 seconds |
| Color visible for sample containing analyte | 3 minutes for strong positive<br>6 minutes for weak positive |

Example 2

The device of example 1 can be simplified by use of a fluorescent label or colored particle e.g. colloidal gold, attached to the chicken anti-heartworm antibody instead of using HRP as the conjugate. In this case, the substrate reagent can be omitted, and the signal is viewed after the unbound reagent is washed away.

Example 3

Figure 7:
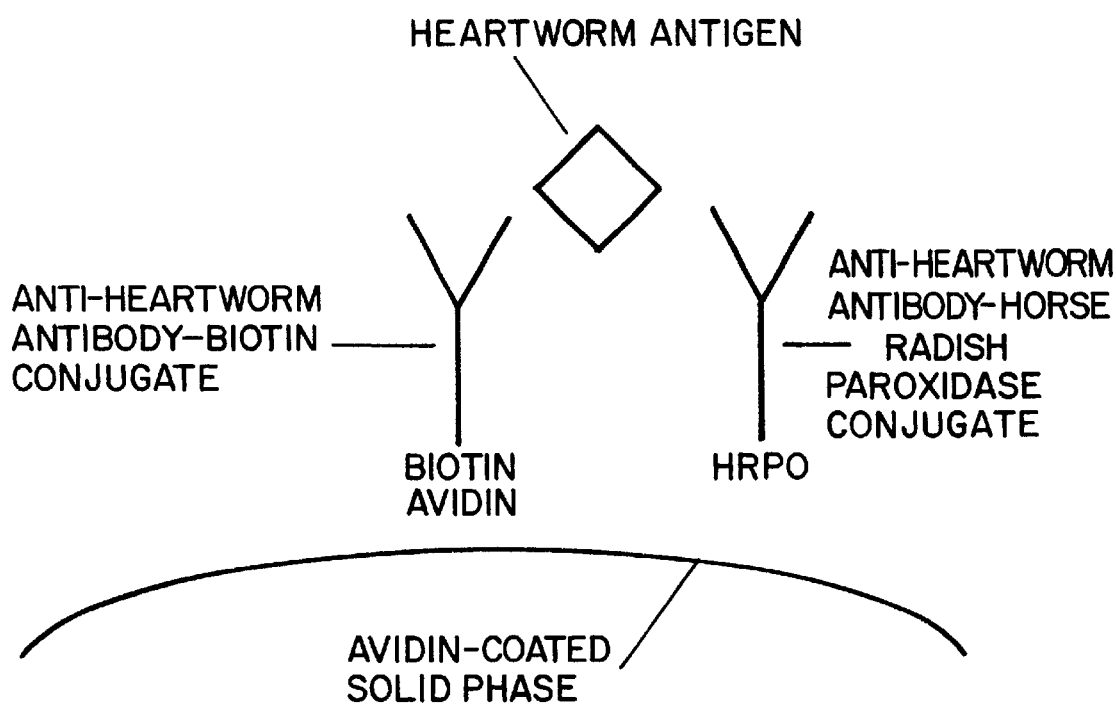
FIG. 7: Schematic depicting assay components for one of the embodiments of the present invention.

To detect multiple analytes in a single sample, a multi-channel device is constructed from the device in example 1 by feeding multiple sample delivery channels from a single sample entry port (FIG. 7). Each sample delivery channel will contain different conjugate binding reagents to detect the different analytes. Thus, four solid-phase containers are constructed to be adjacent to each other. The assembly is attached to a plastic part with four sample delivery channels.

What is claimed is:

1. A device for performing an assay which determines a presence or quantity of an analyte in a liquid sample (1) using a solid phase for capturing said analyte or the analyte bound to a binding partner for the analyte, and (2) detecting binding of said analyte or said analyte bound to its binding partner after washing unbound material from said solid phase, said device comprising:
    (a) a first flow path for sample entry and delivery to a solid phase zone (c);
    (b) a second flow pot comprising a fluid path material, said fluid path material essentially impermeable to said liquid sample, but which defines a second flow path for said sample when made permeable by contact with a wash reagent, wherein said second flow path is independent of said first flow path;
    (c) a solid phase zone permeable to said liquid sample, at an intersection between said first and second flow paths, wherein said solid phase zone comprises a binding partner for said analyte or said analyte bound to its binding partner, and said solid phase is used in both capture and detection of said analyte or said analyte bound to its binding partner,
    whereby said liquid sample initially flows only along said first flow path into said sold phase zone but not into said fluid path material until said fluid path material is rendered hydrophilic by introduction of said wash reagent into said second flow path, whereby said wash reagent removes unbound material from said solid phase zone through said second flow path; and
    (d) a means to test a single sample for a single analyte or a means to test a single sample for multiple analytes.

2. Device of claim 1 wherein said first flow path is through a capillary space called a sample delivery channel.

3. Device of claim 1 wherein said first flow path comprises a bibulous material.

4. Device of claim 1 wherein said first flow path is through a sample delivery channel containing dried conjugate soluble binding reagents.

5. Device of claim 1 wherein said binding partners for the assays include antigens, antibodies, ligands, receptors, nucleic acid molecules, chemical reactants, and fragments thereof.

6. Device of claim 1 further comprising conjugate soluble binding reagents dried in the sample delivery channel.

7. Device of claim 1 further comprising at least one conjugate soluble binding reagent added to the sample prior to adding said sample to said device.

8. Device of claim 1 wherein the assay involves an immobilized reactant or substrate on the solid phase, and detection occurs on said solid phase.

9. Device of claim 1 wherein the assay involves having the reactant or substrate in said first flow path and detection occurs on said solid phase.

10. Device of claim 1 wherein the solid phase is selected from the group consisting of: glass fiber mats, non-woven synthetic mats, sintered particulate structures, cast membrane materials, extruded membrane materials, materials characterized by the presence of adhesion within the material, molded open pore nylon structure, cast open pore nylon structure, molded open pore nitrocellulose structure, cast open pore nitrocellulose structure, particulate material of glass particles, particulate material of polymer particles, and an electrochemical detector.

11. Device of claim 1 wherein said wash reagent is delivered from at least one pierceable container following activation of said device, said wash reagent is selected from the group consisting of at least one wash reagent, at least one substrate reagent, at least one wash reagent and at least one substrate reagent, and at least one wash/substrate reagent.

12. Device of claim 1 further comprising an absorbent block comprised of an absorbent material independent of said fluid path material.

13. Device of claim 1 wherein said second flow path is through bibulous material or plastic.

14. Device of claim 1 further comprising a sample entry port located upstream of the solid phase or directly above the solid phase and sample is applied via a cup structure or a sample absorbing tip.

* * * * *

UNITED STATES PATENT AND TRADEMARK OFFICE
CERTIFICATE OF CORRECTION

PATENT NO.    : 6,436,722 B1
DATED         : August 20, 2002
INVENTOR(S)   : Scott M. Clark et al.

It is certified that error appears in the above-identified patent and that said Letters Patent is hereby corrected as shown below:

<u>Title page,</u>
ABSTRACT,
Line 12, delete "capillary" and replace with -- capillarity --

<u>Column 16,</u>
Line 35, delete "pot" and replace with -- path --.

Signed and Sealed this

Thirty-first Day of December, 2002

JAMES E. ROGAN
*Director of the United States Patent and Trademark Office*